United States Patent [19]

Ferragamo et al.

[11] Patent Number: 5,759,189
[45] Date of Patent: Jun. 2, 1998

[54] KNOT PUSHER

[75] Inventors: Michael C. Ferragamo, N. Dighton; Joseph H. Sklar, Longmeadow, both of Mass.

[73] Assignee: Smith & Nephew Inc., Andover, Mass.

[21] Appl. No.: 804,667

[22] Filed: Feb. 25, 1997

[51] Int. Cl.$^6$ .................................................. A61B 17/04
[52] U.S. Cl. ............................................ 606/148; 606/139
[58] Field of Search ................................ 606/139, 148

[56] References Cited

U.S. PATENT DOCUMENTS

| | | | |
|---|---|---|---|
| D. 353,022 | 11/1994 | Ferragamo | D24/145 |
| D. 359,355 | 6/1995 | Ferragamo | D24/145 |
| D. 360,687 | 7/1995 | Ferragamo | D24/145 |
| D. 360,688 | 7/1995 | Ferragamo | D24/145 |
| 2,595,086 | 4/1952 | Larzelere | 128/326 |
| 3,763,860 | 10/1973 | Clarke | 128/334 |
| 4,602,635 | 7/1986 | Mulhollan et al. | 128/334 |
| 4,923,461 | 5/1990 | Caspari et al. | 606/146 |
| 4,961,741 | 10/1990 | Hayhurst | 606/139 |
| 5,053,043 | 10/1991 | Gottesman et al. | 606/148 |
| 5,084,058 | 1/1992 | Li | 606/148 |
| 5,176,691 | 1/1993 | Pierce | 606/148 |
| 5,192,287 | 3/1993 | Fournier et al. | 606/139 |
| 5,201,744 | 4/1993 | Jones | 606/148 |
| 5,234,445 | 8/1993 | Walker et al. | 606/148 |
| 5,250,054 | 10/1993 | Li | 606/148 |
| 5,269,791 | 12/1993 | Mayzels et al. | 606/148 |
| 5,282,809 | 2/1994 | Kammerer et al. | 606/148 |
| 5,282,811 | 2/1994 | Booker et al. | 606/157 |
| 5,290,300 | 3/1994 | Cosgrove et al. | 606/148 |
| 5,292,327 | 3/1994 | Dodd et al. | 606/148 |
| 5,395,382 | 3/1995 | DiGiovanni et al. | 606/148 |
| 5,397,326 | 3/1995 | Mangum | 606/148 |
| 5,403,330 | 4/1995 | Tuason | 606/148 |
| 5,423,837 | 6/1995 | Miricle et al. | 606/148 |
| 5,472,446 | 12/1995 | de la Torre | 606/148 |

FOREIGN PATENT DOCUMENTS

| | | |
|---|---|---|
| 305885 | 3/1970 | U.S.S.R. . |
| 929090 | 6/1980 | U.S.S.R. . |

OTHER PUBLICATIONS

Bartlett, "Principles of Knot Delivery in Intra-Articular Suturing For Arthroscopic Procedures", American Journal of Arthroscopy, 1:13–15.
Jenson, "Review of Present Treatments for Torn Menisci and Design of New Arthroscopic...", Massachusetts Institute of Technology, 49–51.
"Arthrex Arthroscopy Knot Pusher", Arthrex Brochure, 1991.

*Primary Examiner*—Gary Jackson
*Attorney, Agent, or Firm*—Fish & Richardson P.C.

[57] ABSTRACT

A knot pusher includes a shaft with a distal nose configured for pushing a suture knot. The nose has a surface with a an open suture receiving recess. A securing member is arranged for movement between a closed position and an open position. In its closed position, the securing member at least partially covers the suture receiving recess to prevent removal of a suture therefrom. In its open position, the securing member permits removal of the suture from the suture receiving recess. An actuator moves the securing member between its open and closed positions. The securing member is arranged to slide or pivot relative to the shaft. The securing member is associated with the shaft such that an outer diameter of a distal end of the shaft is not substantially increased with the securing member in its closed position. A method of tying a suture is also described.

15 Claims, 7 Drawing Sheets

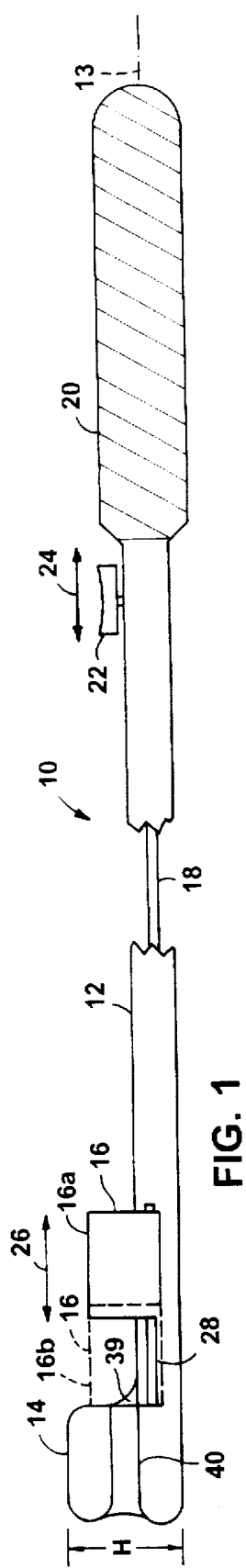
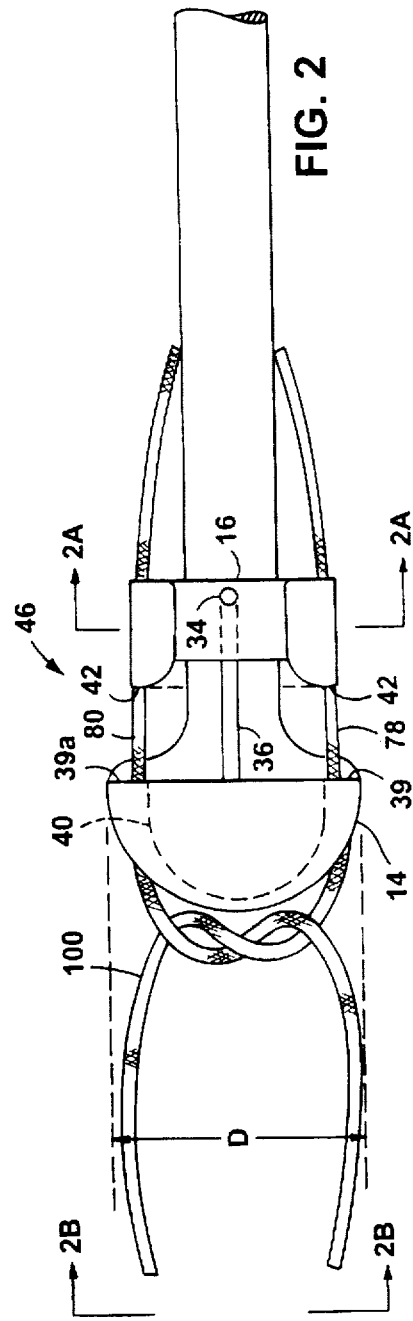
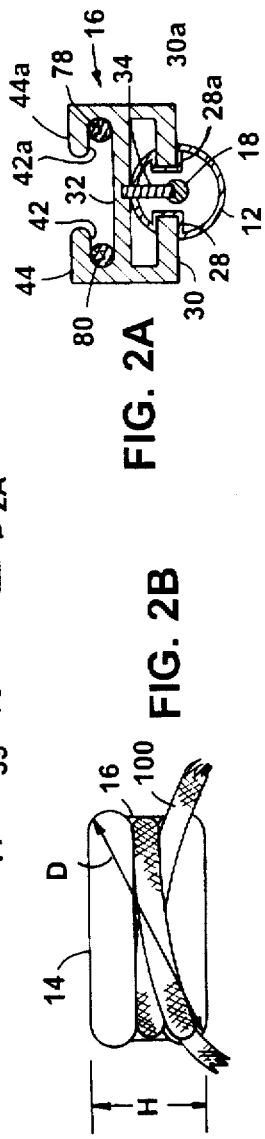
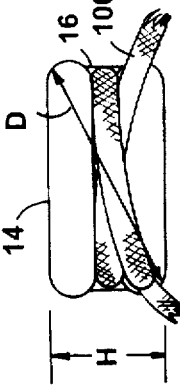

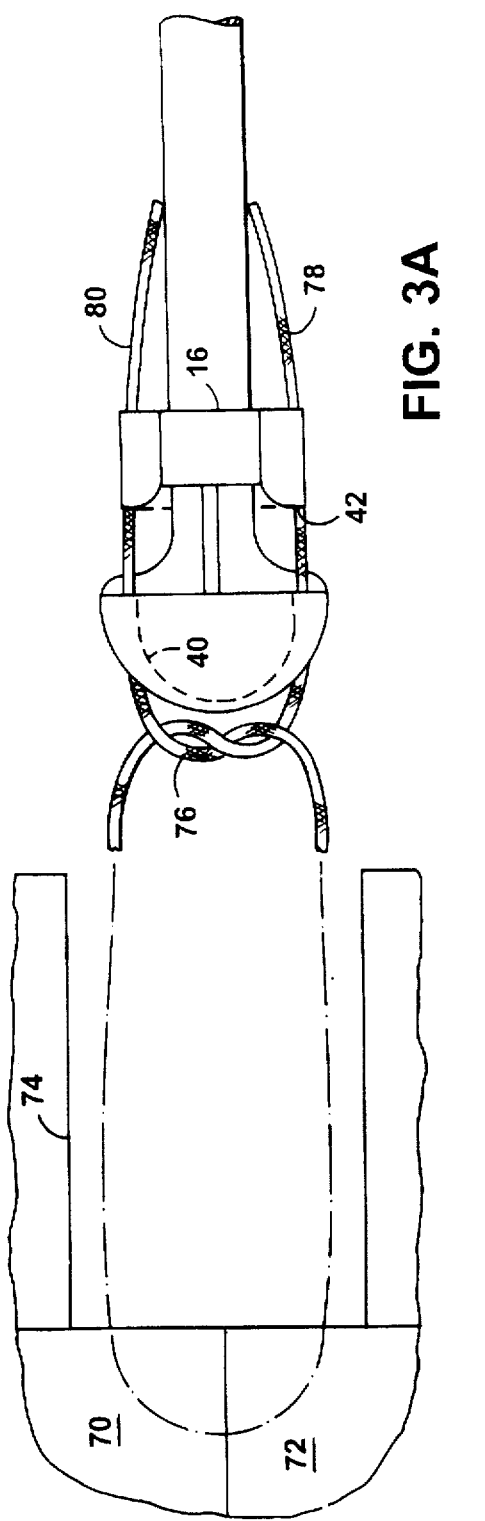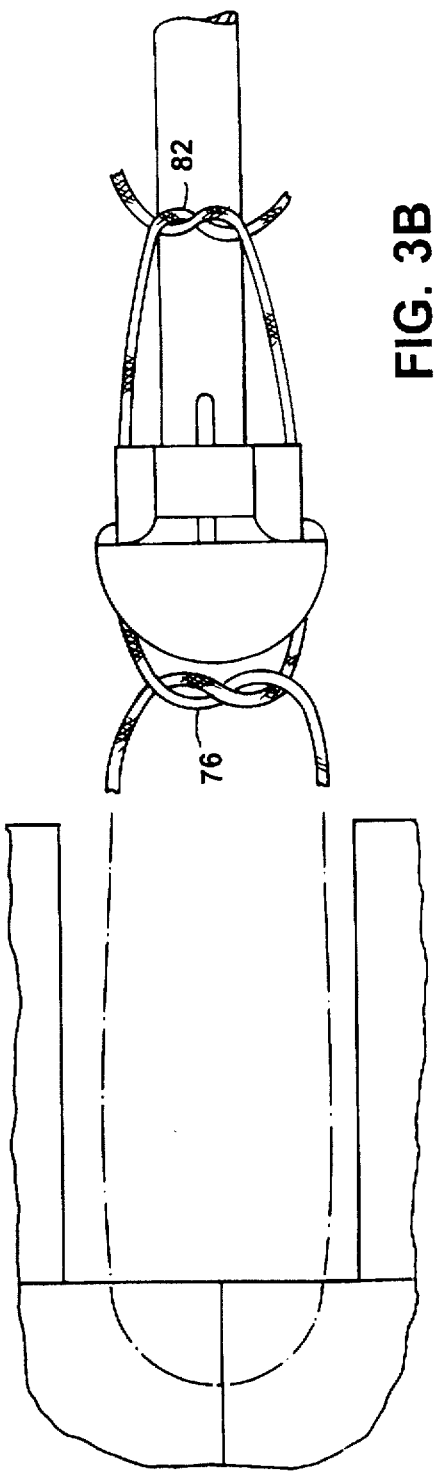
FIG. 3A
FIG. 3B

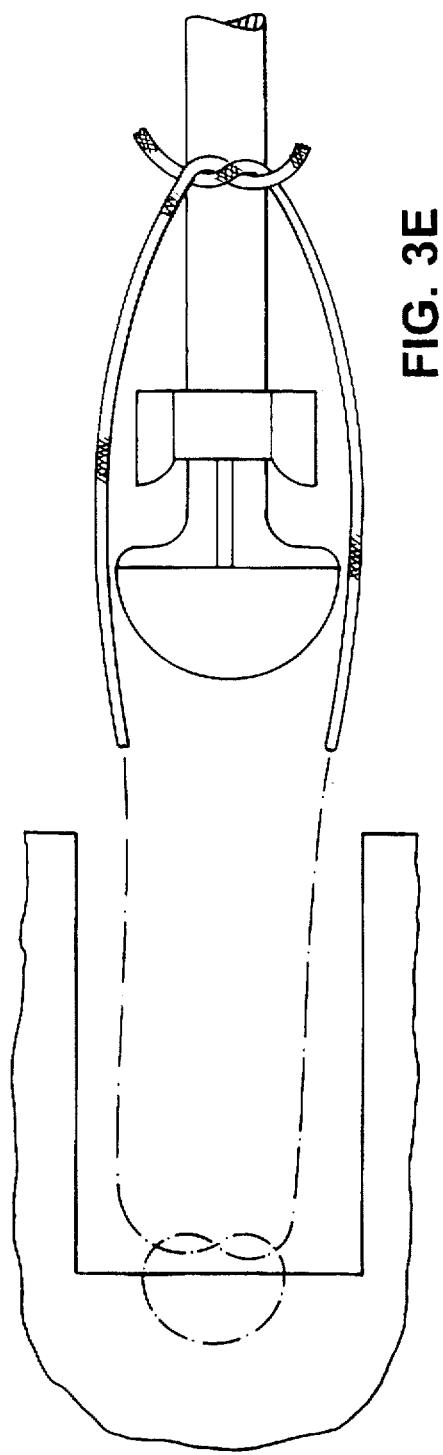
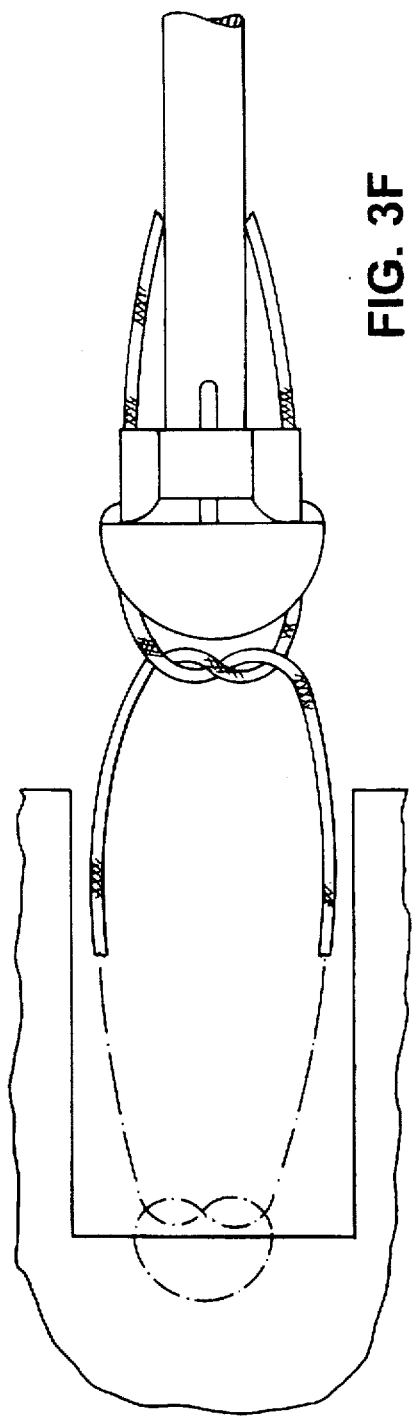
FIG. 3E
FIG. 3F

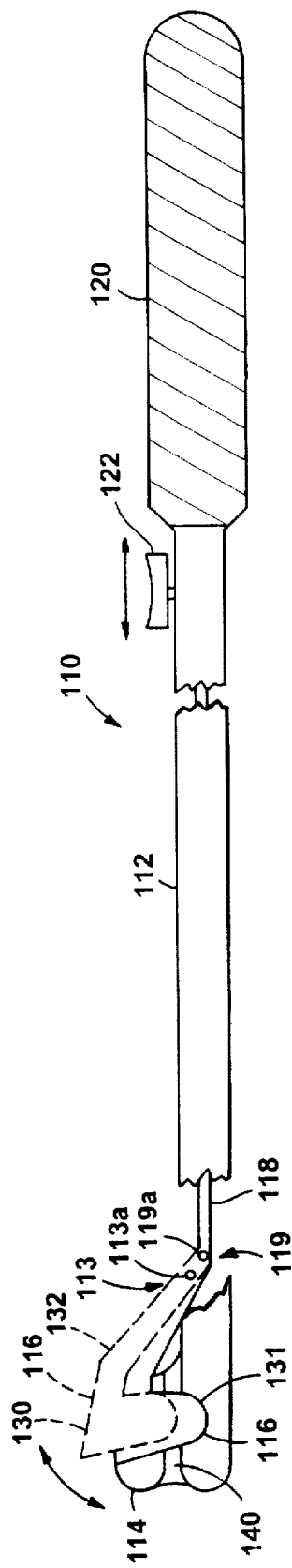
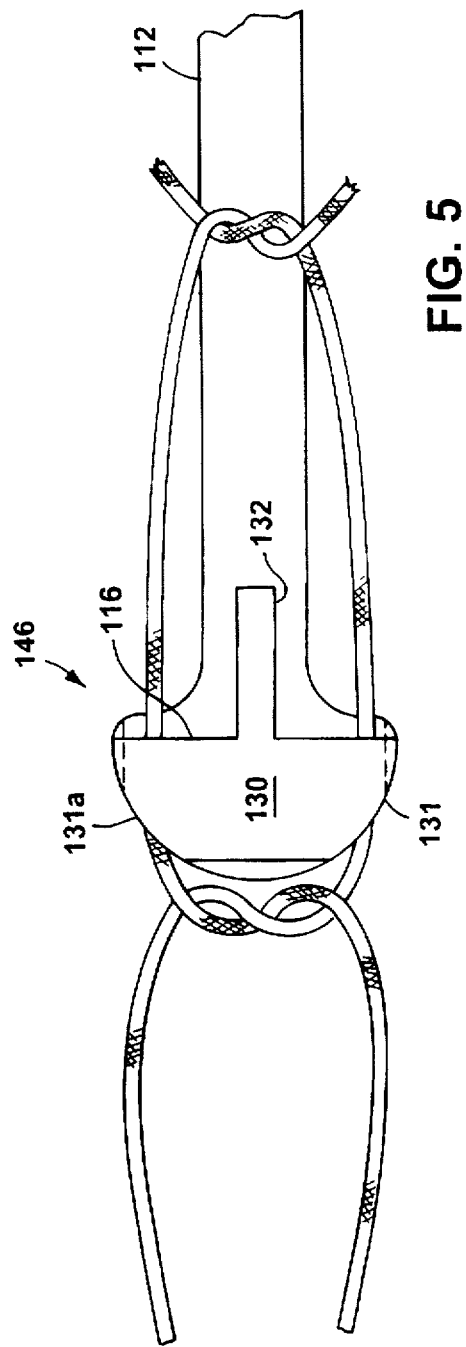

KNOT PUSHER

BACKGROUND OF THE INVENTION

The invention relates generally to surgical instruments and more particularly to knot pushers.

Arthroscopic surgery enables the surgeon to perform surgery without the need to expose the surgical site with a large incision. In order to tie suture knots during arthroscopic surgery, instruments have been developed which permit the surgeon to form a half-knot in a suture outside the surgical site and then push the half-knot through an entry portal to the surgical site. The surgeon repeats the process with a second half-knot to form a knot at the surgical site.

SUMMARY OF THE INVENTION

A knot pusher instrument includes a shaft with a distal nose configured for pushing a suture knot. The nose has a surface with an open suture receiving recess. A securing member is arranged for movement between a closed position and an open position. In its closed position, the securing member at least partially covers the suture receiving recess to prevent removal of a suture therefrom. In its open position, the securing member permits removal of the suture from the suture receiving recess. An actuator moves the securing member between its open and closed positions.

In particular embodiments of the invention, the securing member is arranged to slide relative to the shaft in a direction parallel to a long axis of the shaft. The shaft includes an axial slot and the securing member includes a mounting arm positioned for sliding movement within the slot. Movement of the actuator results in the mounting arm sliding in an axial direction within the slot. A pin fixedly connects the securing member to the actuator. The securing member includes an extension defining a suture receiving section. The securing member, in its closed position, is configured to cover a proximal section of the suture receiving recess.

In other embodiments of the invention, the securing member is arranged to pivot relative to the shaft and includes a proximal extension having a first pivot connector attaching the securing member to the shaft and a second pivot connector attaching the securing member to the actuator. The securing member includes a side extension which, with the securing member in its closed position, at least partially covers the suture receiving recess.

According to another aspect of the invention, the securing member is associated with the shaft such that a transverse outer diameter of a distal end of the shaft is not substantially increased with the securing member in its closed position.

In a method of the invention, a suture is tied by a) tying two free ends of the suture into a first half-knot, b) placing the two free ends into a suture receiving recess of a knot pusher instrument, c) securing the suture, at the recess, for slidable movement, d) tying the two free ends of the suture into a second half-knot, and thereafter e) advancing the instrument to push the first half-knot against tissue being sutured while tensioning the two free ends, f) retracting the instrument, g) releasing the suture from the recess, h) repositioning the instrument proximally of the second half-knot, i) securing the suture, at the recess, for slidable movement, and j) advancing the instrument to push the second half-knot against the first half-knot. The tensioning on the two free ends is maintained during steps e through j.

According to another aspect of the invention, a method of tying a suture includes tying two free ends of a suture into a half-knot, placing the two free ends into a suture receiving recess of a knot pusher instrument, securing the suture, at the recess, for slidable movement, the step of securing substantially maintaining an outer transverse diameter of a distal end of the instrument, and advancing the instrument to push the half-knot against tissue being sutured.

Advantages of the invention include securing the suture to the knot pusher to prevent the suture from slipping out of the knot pusher during advancement of the suture half-knot. The releasable nature of the securing member permits tension to be maintained on the suture during repositioning of the knot pusher proximally of a subsequent half-knot.

BRIEF DESCRIPTION OF THE DRAWINGS

Other objects, features and advantages of the invention will be apparent from the following description taken together with the drawings in which:

FIG. 1 is a side view of a knot pusher, according to the invention;

FIG. 2 is a top view of the knot pusher of FIG. 1;

FIG. 2A shows a securing member of the knot pusher of FIG. 1, taken along lines 2A—2A in FIG. 2;

FIG. 2B is a front view of the knot pusher of FIG. 1, taken along lines 2B—2B in FIG. 2;

FIGS. 3A–3G show the knot pusher of FIG. 1 is use;

FIG. 4 is a side view of an alternate embodiment of a knot pusher according to the invention; and FIG. 5 is a top view of the knot pusher of FIG. 4.

DESCRIPTION OF THE PREFERRED EMBODIMENTS

Figure 3C:
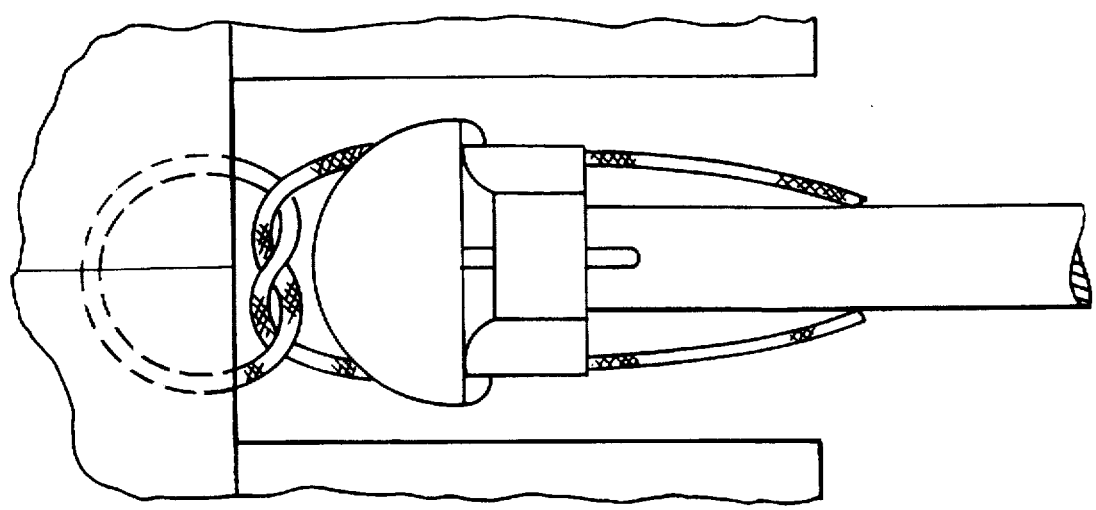

Referring to FIG. 1, a knot pusher 10 for tying a suture knot during, for example, arthroscopic surgery through an entry portal of about 0.5 cm, includes a shaft 12 with a distal nose 14 for pushing a suture knot, a movable securing member 16, and an actuator 18 attached to securing member 16 for moving securing member 16 between an open position 16a (solid lines) and a closed, suture securing position 16b (dashed lines). A handle 20 of knot pusher 10 includes a finger control 22 which is slidable (in the axial direction indicated by arrow 24) relative to handle 20 and is attached to actuator 18 to axially move actuator 18, and thus securing member 16 as well (in the axial direction indicated by arrow 26 parallel to a long axis 13 of shaft 12.)

Referring also to FIGS. 2 and 2A, shaft 12 includes slots 28, 28a for receiving mounting arms 30, 30a, respectively, of securing member 16. Mounting arms 30, 30a attach securing member 16 to shaft 12 and slide within slots 28, 28a as securing member 16 moves between its open and closed positions. Actuator 18 is attached to a cross-bar 32 of securing member 16 with a pin 34. Pin 34 slides within a slot 36 in shaft 12 as securing member 16 moves between its open and closed positions.

Nose 14 includes a circumferential, non-enclosed recess 40 which, during use, receives suture ends 78, 80 of suture 100. Securing member 16 has extensions 44, 44a defining suture receiving sections 42, 42a, respectively. With securing member 16 in its open position, suture ends 78, 80 can be placed into and removed from sections 42, 42a, respectively. With securing member 16 in its closed position, securing member 16 covers proximal sections 39, 39a of recess 40 thus preventing suture ends 78, 80 from slipping out of suture receiving recess 40 while permitting sliding motion of suture 100 within recess 40 and relative to knot pusher 10.

Knot pusher 10 can be used with absorbable and non-absorbable sutures. Securing member 16 can be rigid or flexible, and manufactured from a variety of materials, for example, plastic, Nitinol®, and preferably stainless steel. To mount securing member 16 to shaft 12, mounting arms 30, 30a of securing member 16 are connected to cross-bar 32 after assembly by welding or other known methods.

Referring to FIG. 2B, nose 14 has a transverse diameter, D, of about 0.2 inches and a height, H, of about 0.095 inches, and defines the largest profile of distal end 46 of knot pusher 10. Securing member 16 does not increase the outer profile of distal end 46 thus enabling knot pusher 10 to be used through small arthroscopic portals of, for example, about 0.5 cm.

Referring to FIG. 3A, in use, following arthroscopic suturing of, for example, two tissue segments 70, 72 through a cannula 74, a first half-knot 76 is made in suture ends 78, 80 and the suture ends are placed in nose recess 40 and fed into securing member sections 42. As shown in FIG. 3B, securing member 16 is then pushed distally to secure suture ends 78, 80 within recess 40. A second half-knot 82 is then formed in suture ends 78, 80.

Knot pusher 10 is then advanced through cannula 74 while the surgeon keeps tension on suture ends 78, 80. Knot pusher 10 is advanced until half-knot 76 is against the tissue (FIG. 3C).

Figure 3D:
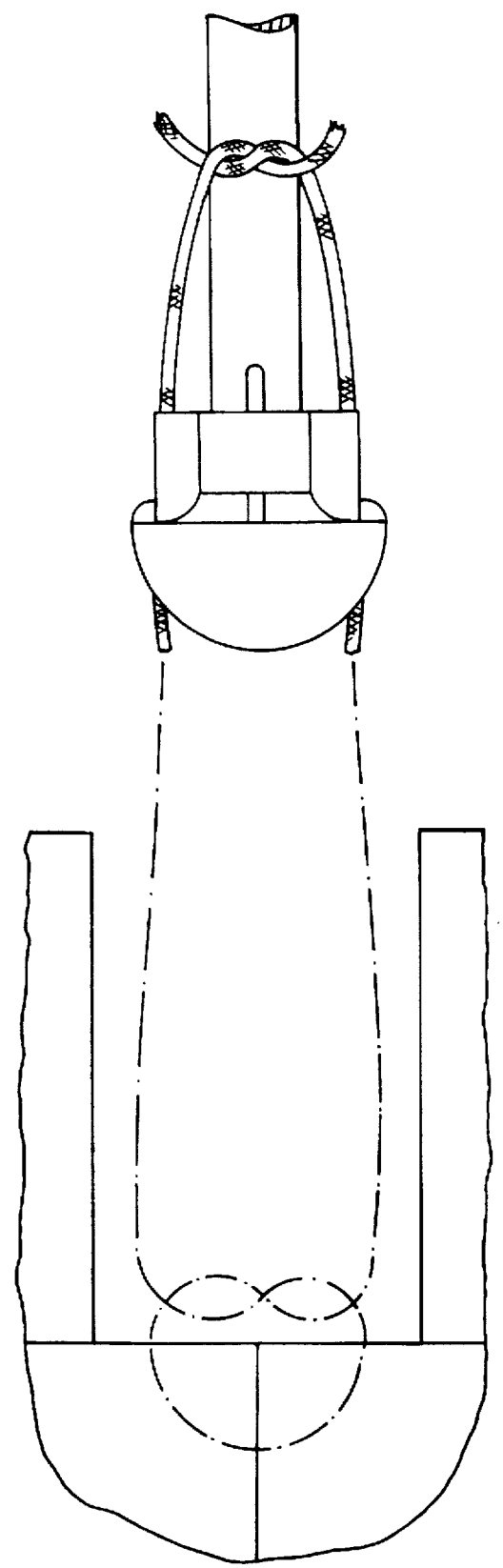
Figure 3G:
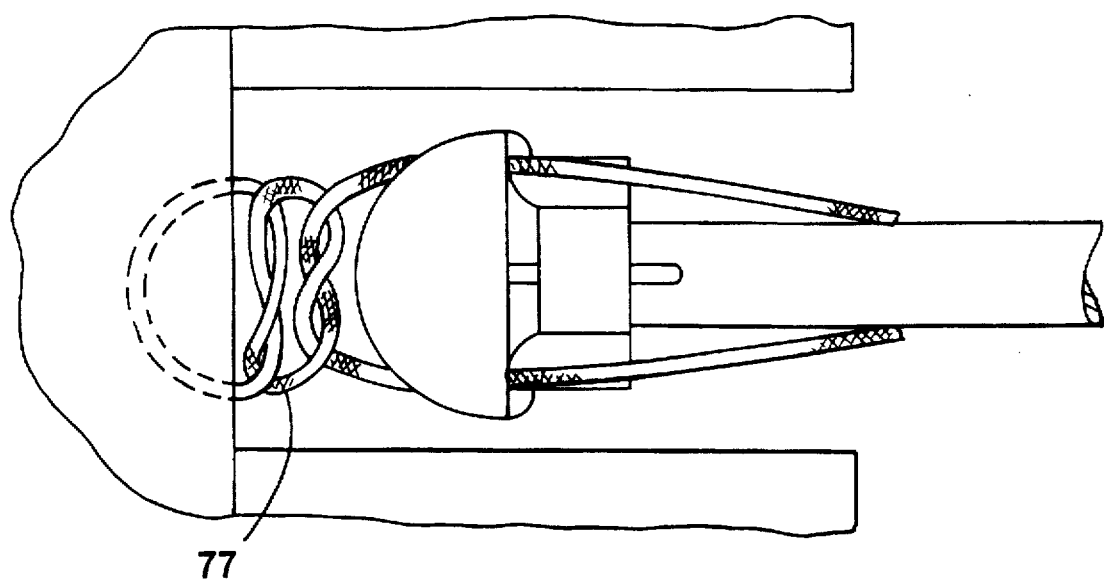

Referring to FIG. 3D, while maintaining tension on suture ends 78, 80 to prevent half-knot 76 from loosening, knot pusher 10 is moved proximally until it is removed from cannula 74. When cleared from the cannula, securing member 16 is opened and suture ends 78, 80 are removed from knot pusher 10 (FIG. 3E). Knot pusher 10 is then placed proximal of second knot 82, suture ends 78, 80 are positioned within nose recess 40 and securing member sections 42 and securing member 16 is closed (FIG. 3F). The surgeon is able to maintain tension on suture ends 78, 80 during the repositioning of knot pusher 10. Knot pusher 10 is then advanced through cannula 74 while the surgeon keeps tension on suture ends 78, 80 until second half-knot 82 is placed against first half-knot 76 (FIG. 3G). The surgeon then tightens the resulting knot 77 and removes knot pusher 10 from cannula 74.

In another embodiment of the invention, referring to FIGS. 4 and 5, instead of a sliding securing member, the securing member of knot pusher 110 is in the form of a pivoting arm 116. Knot pusher 110 includes a shaft 112 having a nose 114, identical to nose 14 described above, an actuator 118, a handle 120 with finger control 122 for moving actuator 118. Arm 116 includes a distal section 130 with side extensions 131, 131a which at least partially cover recess 140 with arm 116 in its closed position, and an attachment member 132 extending proximally from section 130. Member 132 is connected to actuator 118 at a pivot point 119 by a pin 199a and to shaft 112 at a pivot point 113 by a pin 133a. Distal axial movement of actuator 118 by sliding finger control 122 causes arm 116 to open (dashed line), and proximal axial movement of actuator 118 causes arm 116 to close (solid line). With arm 116 closed, suture is secured within a non-enclosed recess 140; with arm 116 opened, suture can be removed from recess 140. Distal section 130 of arm 116 has a thickness in the range of about 0.03 to 0.04 inches such that with arm 116 in its closed position, the outer profile of distal end 146 of knot pusher 110 is not substantially increased thus enabling knot pusher 110 to be used through small arthroscopic portals of, for example, about 0.5 cm. The operation of knot pusher 110 is the same as described above with reference to FIGS. 1, 2 and 3A–3G.

Other embodiments are within the scope of the following claims.

What is claimed is:

1. A knot pusher instrument, comprising:

a shaft including a distal nose configured for pushing a suture knot, a surface of said nose including an open suture receiving recess, a securing member arranged for movement between a closed position and an open position, said securing member in said closed position at least partially covering said suture receiving recess to prevent removal of a suture from said suture receiving recess, said securing member in said open position permitting removal of the suture from said suture receiving recess, and an actuator operatively coupled to said securing member for moving said securing member between said open and closed positions.

2. The knot pusher instrument of claim 1 wherein said securing member is arranged to slide relative to said shaft.

3. The knot pusher instrument of claim 2 wherein said securing member is arranged to slide parallel to a long axis of said shaft.

4. The knot pusher instrument of claim 3 wherein said shaft includes an axial slot and said securing member includes a mounting arm positioned for sliding movement within said slot, movement of said actuator resulting in said mounting arm sliding in an axial direction within said slot.

5. The knot pusher instrument of claim 2 further comprising a pin for fixedly connecting said securing member to said actuator.

6. The knot pusher instrument of claim 2 wherein said securing member includes an extension defining a suture receiving section.

7. The knot pusher instrument of claim 2 wherein said securing member, in said closed position, is configured to cover a proximal section of said suture receiving recess.

8. The knot pusher instrument of claim 1 wherein said securing member is arranged to pivot relative to said shaft.

9. The knot pusher instrument of claim 8 wherein said securing member includes a proximal extension having a first pivot connector attaching said securing member to said shaft and a second pivot connector attaching said securing member to said actuator.

10. The knot pusher instrument of claim 8 wherein said securing member includes a side extension which, with said securing member in said closed position, at least partially covers said suture receiving recess.

11. A knot pusher instrument, comprising:

a shaft including a distal nose configured for pushing a suture knot, a surface of said nose including an open suture receiving recess, said shaft including first and second distal, axially directed, slots, a securing member including a first mounting arm positioned in said first slot and a second mounting arm positioned in said second slot such that said securing member is axially slidable relative to said shaft between a closed position and an open position, said securing member in said closed position covering a proximal section of said suture receiving recess to prevent removal of a suture from said suture receiving recess, said securing member in said open position permitting removal of the suture from said suture receiving recess, and an axially moveable actuator connected to said securing member for moving said securing member between said open and closed positions.

12. A knot pusher instrument, comprising:

a shaft including a distal nose configured for pushing a suture knot, a surface of said nose including an open suture receiving recess, a securing member including a proximal extension having a first pivot connector attaching said securing member to said shaft such that said securing member is pivotable relative to said shaft between a closed position and an open position, and a side extension which, with said securing member in said closed position, at least partially covers said suture receiving recess to prevent removal of a suture from said suture receiving recess, said securing member in said open position permitting removal of the suture from said suture receiving recess, and an actuator attached to a second pivot connector of said securing member for moving said securing member between said open and closed positions.

13. A knot pusher instrument, comprising:

a shaft including a distal nose configured for pushing a suture knot, a surface of said nose including an open suture receiving recess, and a securing member operatively coupled to said shaft and arranged for movement between a closed position and an open position, said securing member in said closed position preventing removal of the suture from said suture receiving recess, said securing member in said open position permitting removal of the suture from said suture receiving recess, said securing member being associated with said shaft such that an outer transverse diameter of a distal end of said shaft is not substantially increased with said securing member in its closed position.

14. A method of tying a suture, comprising the steps of:

a) tying two free ends of a suture into a first half-knot, b) placing said two free ends into a suture receiving recess of a knot pusher instrument, c) securing the suture, at said recess, for slidable movement, d) tying the two free ends of the suture into a second half-knot, and thereafter e) advancing said instrument to push the first half-knot against tissue being sutured while tensioning said two free ends, f) retracting said instrument, g) releasing said suture from said recess, h) repositioning said instrument proximally of said second half-knot, i) securing the suture, at said recess, for slidable movement, and j) advancing said instrument to push the second half-knot against the first half-knot, said tensioning on said two free ends being maintained during steps e through j.

15. A method of tying a suture, comprising the steps of:

tying two free ends of a suture into a half-knot, placing said two free ends into a suture receiving recess of a knot pusher instrument, securing the suture, at said recess, for slidable movement by moving a securing member from an open position to a closed position, said step of securing substantially maintaining a transverse outer diameter of a distal end of said instrument, and advancing said instrument to push the half-knot against tissue being sutured.

* * * * *